(12) United States Patent
Xu

(10) Patent No.: US 9,969,718 B2
(45) Date of Patent: May 15, 2018

(54) PREPARATION METHOD FOR BEMACICLB

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days. days.

(21) Appl. No.: 15/643,837

(22) Filed: Jul. 7, 2017

(65) Prior Publication Data

US 2017/0305884 A1 Oct. 26, 2017

Related U.S. Application Data

(63) Continuation of application No. PCT/CN2016/070013, filed on Jan. 4, 2016.

(30) Foreign Application Priority Data

Jan. 9, 2015 (CN) .......................... 2015 1 0012475

(51) Int. Cl.
C07D 401/14 (2006.01)
C07D 235/08 (2006.01)

(52) U.S. Cl.
CPC ......... *C07D 401/14* (2013.01); *C07D 235/08* (2013.01)

(58) Field of Classification Search
CPC .................................................. C07D 235/08
See application file for complete search history.

(56) References Cited

FOREIGN PATENT DOCUMENTS

CN 102264725 A 11/2011
WO 03030909 A1 4/2003

*Primary Examiner* — Brian E McDowell
(74) *Attorney, Agent, or Firm* — Perkins Coie LLP

(57) ABSTRACT

Disclosed is an intermediate of bemaciclib (also referred to as abemaciclib) having a structure of Formula II,

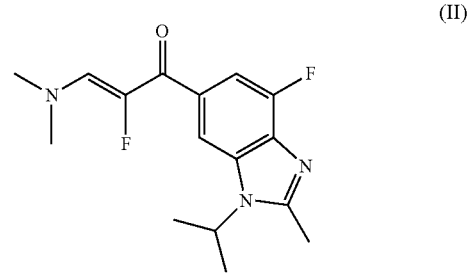

(II)

and preparation methods therefor. The preparation methods may comprise condensation, amidine reaction, cyclization and/or other unit reactions. Bemaciclib is obtained through a guanidination reaction and a cyclization reaction using the bemaciclib intermediate disclosed herein as a starting material. starting materials for the preparation methods disclosed herein are easily available, the procedures are simple, and the preparation methods are economical, environmentally friendly and suitable for industrial production.

1 Claim, No Drawings

PREPARATION METHOD FOR BEMACICLB

CROSS REFERENCE TO RELATED APPLICATIONS

This application is a continuation of PCT/CN2016/070013 filed Jan. 4, 2016, which claims priority to CN 2015100124757 filed Jan. 9, 2015, both of which are incorporated herein by reference.

TECHNICAL FIELD

This invention belongs to the technology field of organic synthetic route design and preparation of its active pharmaceutical ingredients and intermediates, which particularly relates to the preparation method of Bemaciclib, a drug used for treatment of breast cancer.

BACKGROUND ART

Bemaciclib (also known as Abemaciclib or LY2835219), is a drug developed by Eli Lilly Company, and it is used for treatment of breast cancer taking the mechanism of suppressing the CKD 4/6. Phase I clinical data shows that, the mono-therapy of metastatic breast cancer patients with this drug is of relative good curative effect in early period, especially for those hormone-receptor positive breast cancer patients, the clinical benefit rate may be up to 61%, which means that the disease of the patients has been controlled for more than 24 weeks, or the tumor size has been reduced by more than 30%. At present, this drug has entered breast cancer Phase III clinical treatment, and clinical research of non-small cell lung cancer has started as well. As this drug still has no standard translated name in Chinese, the applicant hereby transliterates it to "玻玛西尼".

The chemical name of Bemaciclib is: N-[5-[(4-ethyl-1-piperazine)methyl]-2-pyridyl]-5-fluoro-4-[4-fluoro-2-methyl-1-isopropyl-1H-benzimidazole-6-yl]-2-pyrilamine (I), and its structural formula is:

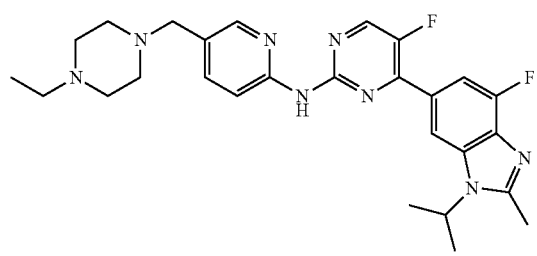

Bemaciclib, I

Preparation of Bemaciclib has already been made research reports, and the reported synthetic route of PCT patent WO2010075074 originally developed by Eli Lilly Company is:

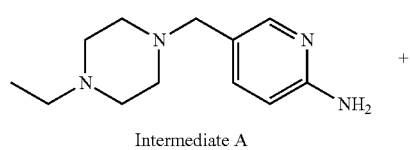

Intermediate A

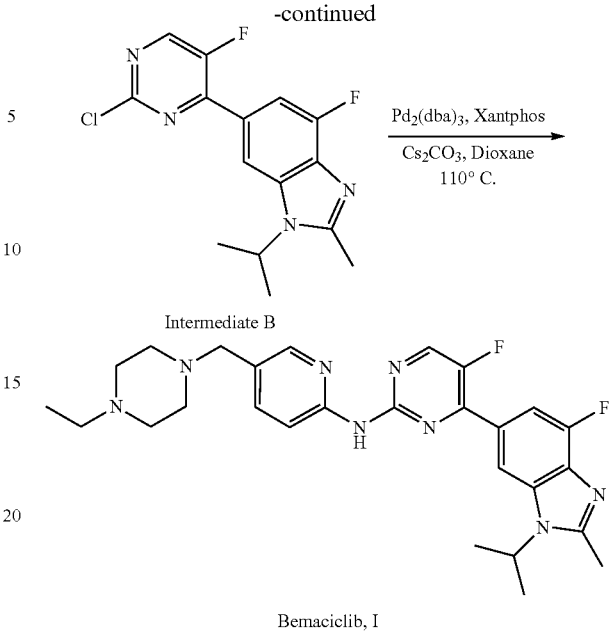

As for intermediate A and intermediate B, under actions of transition metal catalyst tri(dibenzylidene) di-palladium, ligand 4,5-bis (diphenylphosphino)-9,9-dimethyl and its cesium carbonate and others, the "pyridine amidogen" passing through intermediate A and the "pyrimidine halogen" in intermediate B go through substitution reaction, thus obtaining the target product: Bemaciclib.

This patent also reported preparation methods for intermediate A and B. Including, by virtue of condensation and reduction reaction between ethylpiperazine and 2-bromine-4-pyridylaldehyde under reducing agent, the "halogen bromine" in intermediate 1-(2-bromine-4-picolyl)-4-ethylpiperazine obtained and the "ammonia" go through ammonolysis reaction again under actions of metallic copper catalyst, thus intermediate A: 5-[(4-ethyl-piperazine-1-yl) methyl]-2-aminopyridine is finally well prepared.

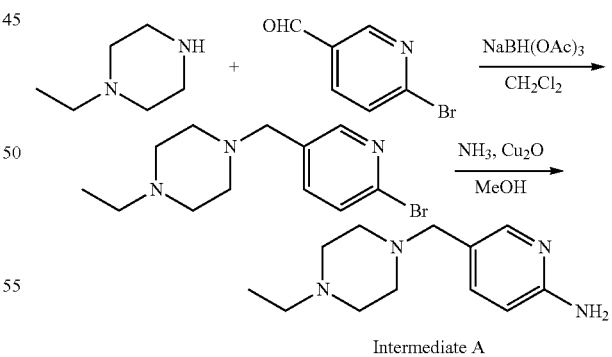

In terms of intermediate B: 2,6-difluoro-4-bromaniline and N-isopropylacetamide go through amidine reaction under actions of chlorinating agent phosphorus oxychloride and acid-binging agent, and generate N-(2,6-difluoro-4-bromine-phenyl)-N'-isopropyl-ethanamidine, and such intermediate goes through cyclization reaction under potassium tert-butoxide, and generates 6-bromine-4-fluorine-1-isopropyl-2-methyl-1H-benzimidazole, and derivatives of such benzimidazole and the bis(pinacolato)diboron form borate ester compounds of derivatives of such benzimidazole under actions of palladium acetate and tricyclohexylphosphine, etc. And then such borate ester compounds and the 2,4-dichloro-4-fluoropyrimidine go through Suzuki reaction under actions of palladium catalyst, thus obtaining the intermediate B: 6-(2-chlorine-5-fluoro-pyrimidine-4-yl)-4-fluorine-1-isopropyl-2-methyl-1H-benzimidazole.

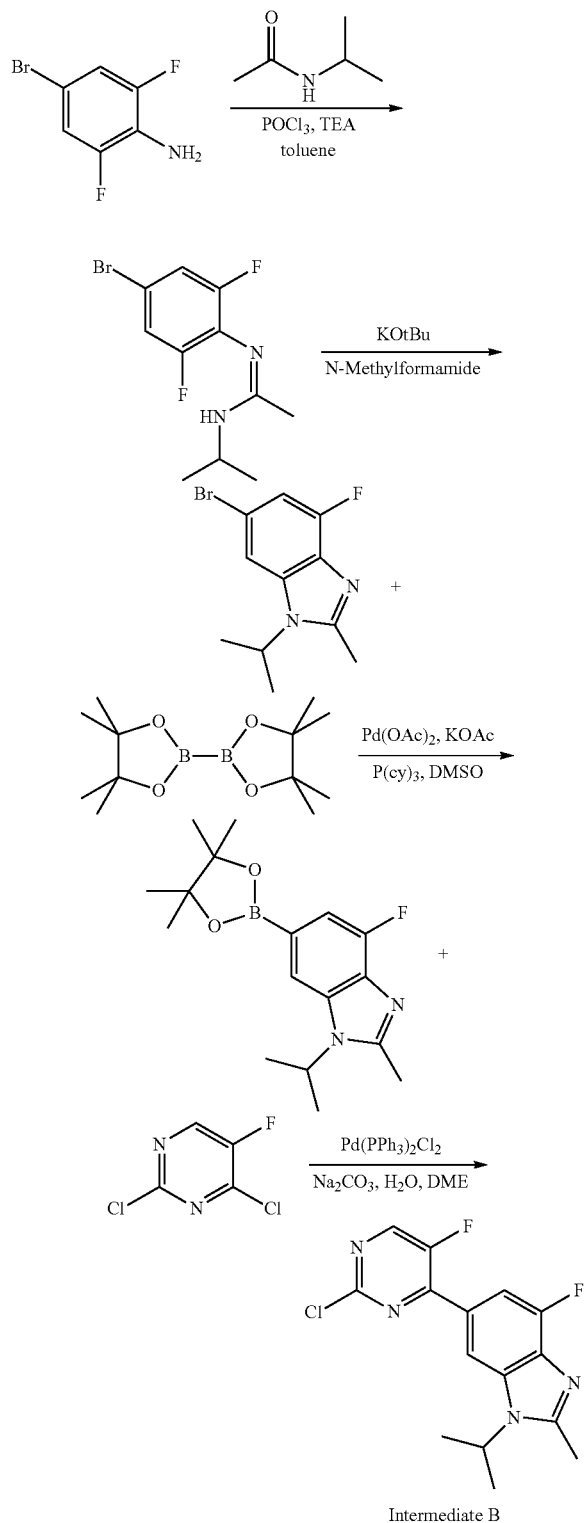

Analyzing the above-mentioned synthetic route, the synthetic thought applied is the method of gradual increment of functional groups, especially that during preparation of intermediate B and its target products, precious metal palladium catalyst and other special ligands are applied in many places, which makes the preparation cost hard to control. Meanwhile, during preparation process of intermediate B and its target products, there has been the circumstance of "several active functional groups compete for the same reaction" in many places, for example, the two chlorine atoms and the one fluorine atom on pyrimidine ring when making Suzuki reaction, and the one chlorine atom and the two fluorine atoms in intermediate B when intermediate A and B make condensation coupling, will all generate potential side reaction due to low selectivity, thus influencing both the quality and yield of the products. Therefore, with respect to the defects of the current processes, developing a simple and direct, economic and environment-friendly Bemaciclib technology with high quality, particularly seeking a process technology that is adaptable to the industrialized production, is of great realistic significance to the improvement of the drug's economic and social benefits.

SUMMARY OF THE INVENTION

This invention aims to provide an economic and environment-friendly preparation method for Bemaciclib intermediates and Bemaciclib, which is suitable for industrialized production and has good availability of raw materials and simple and direct processes.

To achieve the above-mentioned purposes, the invention provides the following main technical scheme: a preparation method for Bemaciclib intermediates. Its chemical name is 6-(3-N,N-dimethylammonium-2-fluoro-2-propylene-1-yl)-4-fluoro-1-isopropyl-2-methyl-1H-benzimidazole, and the chemical formula is as shown in the formula (II):

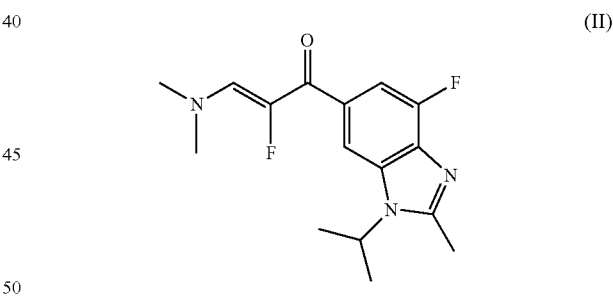

(II)

Its preparation method I comprises the following steps: 1-(4-amidogen-2,6-difluoro-phenyl)-2-fluoro-ethanone (III) and N,N-dimethylformamide dimethyl acetal (DMF-DMA) go through a first condensation reaction to obtain 1-(4-amidogen-2,6-difluoro-phenyl)-3-N,N-dimethylammonium-2-fluoro-2-acrylketone (IV); 1-(4-amidogen-2,6-difluoro-phenyl)-3-N,N-dimethylammonium-2-fluoro-2-acrylketone (IV) and N-isopropylacetamide go through a first amidine reaction under actions of a first halogenating agent and a first acid-binding agent to obtain N-[2,6-difluoro-4-(3-N,N-dimethylammonium-2-fluoro-2-acrylketone-1-yl)phenyl]-N'-isopropyl-ethanamidine (V); N-[2,6-difluoro-4-(3-N,N-dimethylammonium-2-fluoro-2-acrylketone-1-yl)phenyl]-N'-isopropyl-ethanamidine (V) goes through a first cyclization reaction under actions of a first alkali accelerant to obtain bemaciclib intermediate 6-(3-N,N-dimethylammonium-2-fluoro-2-acrylketone-1-yl)-4-fluoro-1-isopropyl-2-methyl-1H-benzimidazole (II).

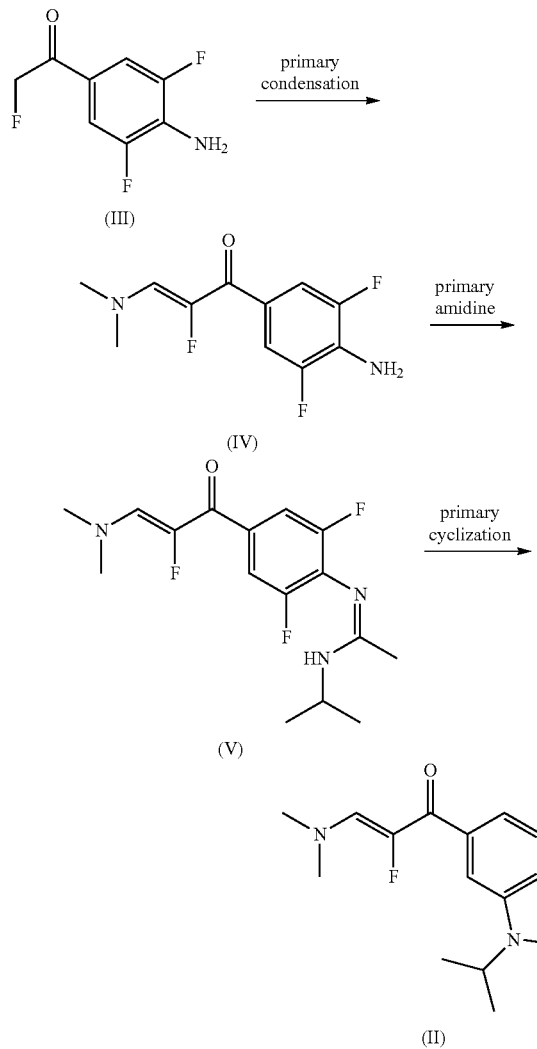

Molar ratio of raw materials of the aforesaid primary condensation reaction, 1-(4-amidogen-2,6-difluoro-phenyl)-2-fluoro-ethanone (III) and DMF-DMA is: 1:2-6, and 1:3-5 is preferred, and 1:4 is more preferred.

Temperature of aforesaid primary condensation reaction is 55-180° C., and 140-150° C. is preferred.

Solvents of the aforesaid primary condensation reaction are methylbenzene, xylene, dioxane, 1,2-dichloroethane, dimethyl-sulfoxide or N,N-dimethylformamide (DMF), and xylene, or DMF is preferred.

Molar ratio of raw materials of the aforesaid primary amidine reaction, 1-(4-amidogen-2,6-difluoro-phenyl)-3-N,N-dimethylammonium-2-fluoro-2-acrylketone (IV) and N-isopropylacetamide is 1:1-3, and 1:2 is preferred.

Primary halogenating agents of the aforesaid primary amidine reaction are phosphorus oxychloride, phosphorus trichloride, phosphorus pentachloride, phosphorus tribromo, thionyl chloride, and phosphorus oxychloride is preferred.

Primary acid-binding agents of the aforesaid primary amidine reaction are triethylamine, pyridine, 2,6-lutidine, 4-dimethylaminopyridine (4-DMAP), N,N-diisopropylethylamine, N-methylmorpholine, N-ethylmorpholine, diisopropylethylamine, 1,5-diazabicyclo [4.3.0] non-5-ene, 1,8-diazabicyclo[5.4.0] eleven-7-ene or 1,4-diazabicyclo[2.2.2]octane, triethylamine or N,N-diisopropylethylamine is preferred.

Temperature of the aforesaid primary amidine reaction is 55-140° C., and 105-115° C. is preferred.

Solvents of the aforesaid primary amidine reaction are methylbenzene, xylene, dioxane, 1,2-dichloroethane, DMF or dimethyl sulfoxide, and methylbenzene is preferred.

Primary alkaline accelerants of the aforesaid primary cyclization reaction are cesium carbonate, potassium carbonate, potassium tert-butoxide, sodium tert-butoxide, sodium methoxide, sodium ethoxide, sodium amid or sodium hydrid, and potassium tert-butoxide or sodium hydrid is preferred.

Temperature of the aforesaid primary cyclization reaction is 100-160° C., and 140-150° C. is preferred.

Solvents of the aforesaid primary cyclization reaction are methylbenzene, xylene, DMF, N,N-dimethylacetamide (DMA), N-methyl pyrrolidone (NMP) or dimethyl sulfoxide, and DMF is preferred.

This invention has also provided preparation method II for preparing the Bemaciclib intermediate 6-(3-N,N-dimethyl ammonium-2-fluoro-2-acrylketone-1-yl)-4-fluoro-1-isopropyl-2-methyl-1H-benzimidazole (II), and the preparation method II comprises the following steps: 1-(4-amidogen-2,6-difluoro-phenyl)-2-fluoro-ethanone (III) and N-isopropylacetamide go through secondary amidine reaction under actions of secondary acid-binding agents to form N-[2,6-difluoro-4-(2-fluoro-ethanone-1-yl)phenyl]-N'-isopropyl-ethanamidine (VI); and N-[2,6-difluoro-4-(2-fluoro-ethanone-1-yl)phenyl]-N'-isopropyl-ethanamidine (VI) goes through secondary cyclization reaction under actions of secondary alkali accelerant to obtain 6-(2-fluoro-ethanone-1-yl)-4-fluoro-1-isopropyl-2-methyl-1H-benzimidazole (VII); and 6-(2-fluoro-ethanone-1-yl)-4-fluoro-1-isopropyl-2-methyl-1H-benzimidazole (VII) and DMF-DMA go through secondary condensation reaction to obtain Bemaciclib intermediate 6-(3-N,N-dimethylammonium-2-fluoro-2-acrylketone-1-yl)-4-fluoro-1-isopropyl-2-methyl-1H-benzimidazole (II).

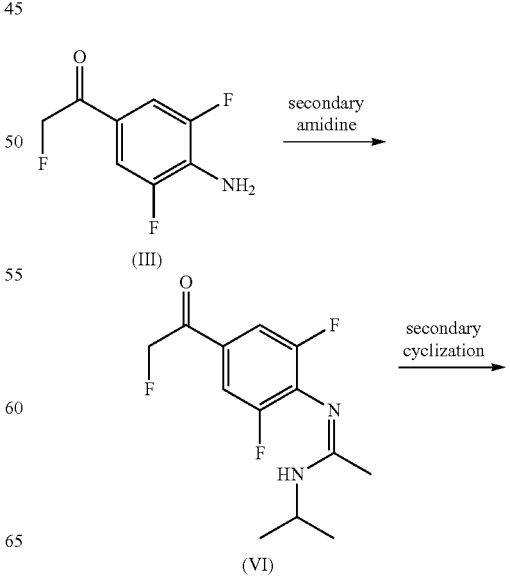

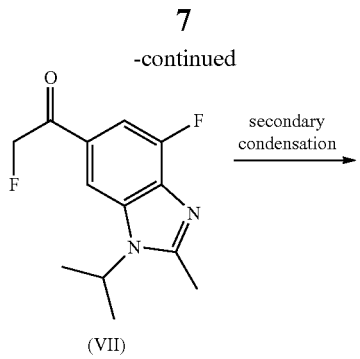

(VII)

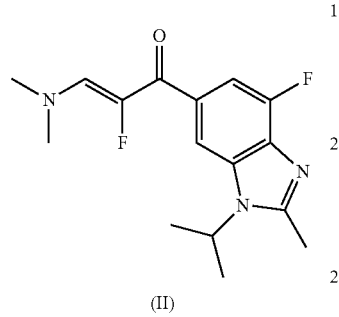

(II)

Molar ratio of raw materials of the aforesaid secondary amidine reaction, 1-(4-amidogen-2,6-difluoro-phenyl)-2-fluoro-ethanone (III) and N-isopropylacetamide is 1:1-3, and 1:2 is preferred.

Secondary halogenating agents of the aforesaid secondary amidine reaction are phosphorus oxychloride, phosphorus trichloride, phosphorus pentachloride, phosphorus tribromo, thionyl chloride, and phosphorus oxychloride is preferred.

Secondary acid-binding agents of the aforesaid secondary amidine reaction are triethylamine, pyridine, 2,6-lutidine, 4-DMAP, N,N-diisopropylethylamine, N-methylmorpholine, N-ethylmorpholine, diisopropylethylamine, 1,5-diazabicyclo [4.3.0]-non-5-ene, 1,8-diazabicyclo[5.4.0]-eleven-7-ene or 1,4-diazabicyclo[2.2.2] octane, triethylamine or N,N-diisopropylethylamine is preferred.

Temperature of the aforesaid secondary amidine reaction is 70-130° C., and 95-105° C. is preferred.

Solvents of the aforesaid secondary amidine reaction are methylbenzene, xylene, dioxane, 1,2-dichloroethane, or dimethyl sulfoxide, and dioxane is preferred.

Secondary alkali accelerants of the aforesaid secondary cyclization reactions are cesium carbonate, potassium carbonate, potassium tert-butoxide, sodium tert-butoxide, sodium methoxide, sodium ethoxide, sodium amid or sodium hydrid, and potassium tert-butoxide or sodium hydrid is preferred.

Temperature of the aforesaid secondary cyclization reaction is 90-140° C., and 100-120° C. is preferred.

Solvents of the aforesaid secondary cyclization reaction are methylbenzene, xylene, DMF, DMA, NMP or dimethyl sulfoxide, and methylbenzene is preferred.

Molar ratio of raw materials of the aforesaid secondary condensation reaction, 6-(2-fluoro-ethanone-1-yl)-4-fluoro-1-isopropyl-2-methyl-1H-benzimidazole (VII) and DMF-DMA is: 1:2-6, and 1:3-5 is preferred, and 1:4 is more preferred.

Temperature of the aforesaid secondary condensation reaction is 50-150° C., and 120-130° C. is preferred.

Solvents of the aforesaid secondary condensation reaction are methylbenzene, xylene, dioxane, 1,2-dichloroethane, dimethyl sulfoxide or DMF, and xylene or DMF is preferred.

In addition, the second purpose of this invention is to provide a method for preparing Bemaciclib (I) taking the aforesaid Bemaciclib intermediate 6-(3-N,N-dimethylammonium-2-fluoro-2-acrylketone-1-yl)-4-fluoro-1-isopropyl-2-methyl-1H-benzimidazole (II) as raw materials, and similarly, this preparation method is also of simple and direct process, mild conditions and less side reactions, and is fit for requirement for industrialized enlargement.

English name of the above-mentioned 坡玛西尼 is Bemaciclib, and the chemical name is: N-[5-[(4-ethyl-1-piperazine)methyl]-2-pyridyl]-5-fluoro-4-[4-fluoro-2-methyl-1-isopropyl-1H-benzimidazole-6-yl]-2-pyrilamine (I), the chemical structural formula is as follow:

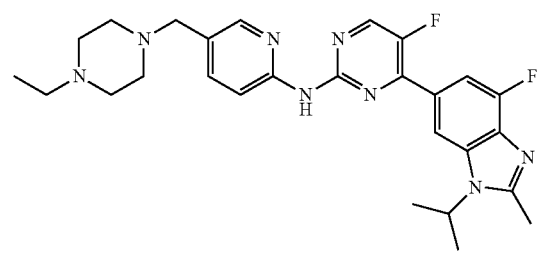

Bemaciclib, I

Preparation method of the above-mentioned Bemaciclib comprises the following steps: make 5-(4-ethyl-piperazine-1-yl-methyl)-2-aminopyridine (VIII) and cyanamide go through guanidination reaction to form N-[5-(4-ethyl-piperazine-1-yl-methyl)pyridine-2-yl]guanidine nitrate (IX); and N-[5-(4-ethyl-piperazine-1-yl-methyl)pyridine-2-yl] guanidine nitrate (IX) and 6-(3-N,N-dimethylammonium-2-fluoro-2-acrylketone-1-yl)-4-fluoro-1-isopropyl-2-methyl-1H-benzimidazole (II) go through tertiary cyclization reaction under actions of tertiary alkali accelerants to obtain Bemaciclib (I).

VIII

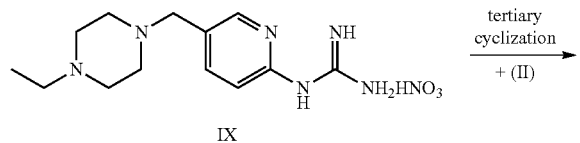

IX

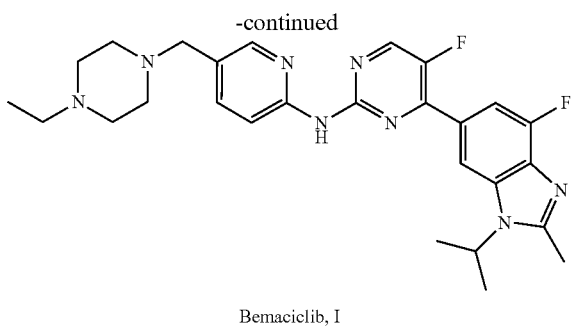

Bemaciclib, I

Temperature of the aforesaid guanidination reaction is 50-100° C., and 75-85° C. is preferred.

Solvents of the aforesaid guanidination reaction are tetrahydrofuran, acetonitrile, methanol, ethyl alcohol, ethyl alcohol, isopropanol, n-butanol or methylbenzene, and ethyl alcohol is preferred.

Molar ratio of raw materials of the aforesaid tertiary cyclization reaction, N-[5-(4-ethyl-piperazine-1-yl-methyl) pyridine-2-yl]guanidine nitrate (IX) and 6-(3-N,N-dimethylammonium-2-fluoro-2-acrylketone-1-yl)-4-fluoro-1-isopropyl-2-methyl-1H-benzimidazole (II) is 1:05-1.5, and 1:0.9-1.1 is preferred.

Tertiary Alkali accelerants of the aforesaid tertiary cyclization reaction are sodium hydroxide, potassium hydroxide, potassium carbonate, cesium carbonate, sodium methoxide or sodium ethoxide, and sodium hydroxide or potassium hydroxide is preferred.

Temperature of the aforesaid tertiary cyclization reaction is 60-130° C., and 90-100° C. is preferred.

Solvents of the aforesaid tertiary cyclization reaction are methylbenzene, acetonitrile, tetrahydrofuran, methanol, ethyl alcohol, n-butanol, isopropanol or tert-butyl alcohol, and n-butanol is preferred.

Compared to the existing technologies, the preparation method for Bemaciclib (I) involved in this invention features good availability of raw materials, simple and direct processes and economy and environmental protection, which thus is beneficial to the industrialized production of the active pharmaceutical ingredients, and can promote its economic and technical development.

DETAILED DESCRIPTION OF THE PREFERRED EMBODIMENTS

A detailed and unrestricted description is further made as follows against the technical scheme of this invention in combination with several preferred embodiments.

For preparation of the raw materials 1-(4-amidogen-2,6-difluoro-phenyl)-2-fluorine-ethanone (III), see "Tetrahedron 64 (2008) 7318-7323" or "Tetrahedron Letters 52 (2011) 5170-5172" for preparation methods of the same compounds; for preparation method of the raw materials, 5-(4-ethyl-piperazine-1-yl-methyl)-2-aminopyridine (VIII), see the Patent No. WO2010075074 (publication date: Jul. 1, 2010) for preparation methods of the same compounds.

Embodiment I [Preparation of Raw Materials III]:

Add 1-(4-amidogen-2,6-difluoro-phenyl) ethanone (3.4 g, 20 mmol), fluorinating agent 1-chloromethyl-4-fluorine-1,4-diazotization bicyclic [2.2.2] octane di(tetrafluoroborate) (F-TEDA-$BF_4$) (14.2 g, 40 mmol) and methanol 50 mL into the reaction flask, and raise the temperature to backflow and continue the reaction for 48 hours, and detect the end of reactions with TLC. Remove the methanol by pressure distillation, and use 150 mL dichlormethane to dissolve the leftovers, and wash and concentrate the reaction system with water and saturated sault solution respectively, and then add 15 mL dichlormethane, 3 mL trifluoroacetic acid and 3 mL water to the grease obtained, and after stirring under room temperature for 1 hour, regulate it to the neutral nature with saturated sodium bicarbonate solution, make twice extractions of dichlormethane, combine the organic phase, and use anhydrous sodium sulfate for drying and concentration, and recrystallize the obtained crude products with n-hexane and ethyl acetate (5:1, V/V), and dry it by vacuum to obtain the off-white solid, 1-(4-amidogen-2,6-difluoro-phenyl)-2-fluorine-ethanone (III) 3.1 g; the yield rate is 82.0%; and the spectrum (EI): m/z 190 (M+H).

Embodiment II [Preparation of Raw Material III]:

Add 2,6-difluoroaniline (2.6 g, 20 mmol) and fluorineacetonitrile/dichlormethane solution (1M, 40 mL) into the reaction flask, and add trifluoromethanesulfonic acid (15 g, 100 mmol) while stirring, raise the temperature to 50° C., and conduct stirring operations for 12-15 hours, and detect the end of reactions with TLC. Pour in ice water to quench the reaction, and make three times of extractions with dichlormethane, and as for the organic phase, use water, 10% sodium bicarbonate solution and saturated salt solution respectively, and use anhydrous sodium sulfate for dry and concentration, and there will be solid precipitation, and recrystallize the obtained crude products with n-hexane and ethyl acetate (5:2, V/V), dry it by vacuum to obtain the off-white solid, 1-(4-amidogen-2,6-difluoro-phenyl)-2-fluoro-ethanone (III) 3.2 g, the yield rate is 84.7%; mass spectrum (EI): m/z 190 (M+H).

Embodiment III [Primary Condensation Reaction]:

Add 1-(4-amidogen-2,6-difluoro-phenyl)-2-fluoro-ethanone (III) (1.9 g, 10 mmol), DMF-DMA (4.8 g, 40 mmol) and solvent DMF 15 mL into the reaction flask in the nitrogen atmosphere; raise the temperature to 140-150° C., and conduct stirring operations for 8-12 hours, and detect the end of reactions with TLC. Reduce the pressure and recycle the solvent, and recrystallize the obtained yellow grease with ethyl acetate and n-hexane (1:1, V/V), dry it by vacuum to obtain faint yellow solid 1-(4-amidogen-2,6-difluoro-phenyl)-3-N,N-dimethylammonium-2-fluoro-2-acrylketone (IV) 2.2 g, the yield rate is 88.7%; $^1$H NMR (CDCl$_3$) 2.94 (s, 6H), 4.91 (brs, 2H), 6.74 (s, 1H), 7.30 (s, 2H); mass spectrum (EI): m/z 245 (M+H).

Embodiment IV [Primary Amidine Reaction]:

Under nitrogen atmosphere, add 1-(4-amidogen-2,6-difluoro-phenyl)-3-N,N-dimethylammonium-2-fluoro-2-acrylketone (IV) (2.5 g, 10 mmol), N-isopropylacetamide (2.0 g, 20 mmol), phosphorus trichloride (2.0 g, 13 mmol) and methylbenzene 50 mL, 0-5° C., and add triethylamine (2.0 g, 20 mmol) while stirring, and then, raise the temperature to 105-115° C. and conduct stirring operations for 3-5 hours. Reduce the pressure and recycle the solvent, and dissolve the leftovers with dichlormethane 100 mL, and wash with saturated sodium bicarbonate and water, and use anhydrous sodium sulfate for drying and concentration, and obtain yellow solid N-[2,6-difluoro-4-(3-N,N-dimethylammonium-2-fluoro-2-acrylketone-1-yl)phenyl]-N'-isopropyl-ethanamidine (V) 2.8 g, the yield rate is 85.6%; mass spectrum (EI): m/z 328 (M+H).

Embodiment V [Primary Cyclization Reaction]:

Add N-[2,6-difluoro4-(3-N,N-dimethylammonium-2-fluoro-2-acrylketone-1-yl)phenyl]-N'-isopropyl-ethanamidine (V) (3.3 g, 10 mmol) and solvent DMF 30 mL, lower the temperature to 5° C., add potassium tert-butoxide (2.2 g, 20 mmol) while stirring. Raise the temperature to 140-150°

C., and continue the reaction for 2-3 hours, and detect the end of reactions with TLC. Lower the temperature to room temperature, and pour the reaction solution into ice water, and use dichlormethane to make three times of extractions, combine the organic phase, and wash with water and saturated salt solution in turn, and use anhydrous sodium sulfate for drying and concentration until it is dry, and conduct two times of beating and washing of the obtained crude products with n-hexane, and obtain faint yellow solid, 6-(3-N,N-dimethylammonium-2-fluoro-2-acrylketone-1-yl)-4-fluoro-1-isopropyl-2-methyl-1H-benzimidazole (II) 2.5 g, the yield rate is 81.4%; $^1$H NMR (CDCl$_3$) 1.55 (d, 6H), 1.63 (s, 1H), 2.68 (m, 1H), 2.96 (s, 6H), 6.78 (s, 1H), 7.45 (s, 2H); mass spectrum (EI): m/z 308 (M+H).

Embodiment VI [Secondary Amidine Reaction]:

Under nitrogen atmosphere, add 1-(4-amidogen-2,6-difluoro-phenyl)-2-fluoro-ethanone (III) (1.9 g, 10 mmol), N-isopropylacetamide (2.0 g, 20 mmol), phosphorus trichloride (2.0 g, 13 mmol) and dioxane 50 mL, 0-5° C. into the reaction flask, and add N,N-diisopropylethylamine (2.6 g, 20 mmol) while stirring, and then, raise the temperature to 95-105° C., and conduct stirring operations for 3-5 hours. Reduce the pressure and remove the solvent, and dissolve the leftovers with ethyl acetate 100 mL, and wash with saturated sodium bicarbonate and water, and use anhydrous sodium sulfate for drying and concentration, and then obtain off-white solid, N-[2,6-difluoro4-(2-fluorine-ethanone-1-yl) phenyl]-N'-isopropyl-ethanamidine (VI) 2.3 g, the yield rate is 84.6%; mass spectrum (EI): m/z 273 (M+H).

Embodiment VII [Secondary Cyclization Reaction]:

Under nitrogen atmosphere, add N-[2,6-difluoro4-(2-fluoro-ethanone-1-yl)phenyl]-N'-isopropyl-ethanamidine (VI) (2.7 g, 10 mmol) and solvent methylbenzene 30 mL into the dry reaction flask, lower the temperature to 5° C., and add 60% sodium hydrid/kerosene (0.8 g, 20 mmol) while stirring. Raise the temperature to 105-115° C., and continue the reaction for 2-3 hours, and detect the end of reactions with TLC. Lower the temperature to room temperature, pour the reaction solution into ice water to separate the organic phase, and make two twice extractions of water phase with methylbenzene, combine the organic phase, and wash with water and saturated salt solution in turn, and use anhydrous sodium sulfate for drying and concentration until it is dry, and obtain off-white solid, 6-(2-fluoro-ethanone-1-yl)-4-fluoro-1-isopropyl-2-methyl-1H-benzimidazole (VII) 2.1 g, the yield rate is 83.3%; mass spectrum (EI): m/z 253 (M+H).

Embodiment VIII [Secondary Condensation Reaction]:

Add 6-(2-fluoro-ethanone-1-yl)-4-fluoro-1-isopropyl-2-methyl-1H-benzimidazole (VII) (2.5 g, 10 mmol), DMF-DMA (4.8 g, 40 mmol) and solvent xylene 25 mL into the reaction flask, and raise the temperature slowly to 120-130° C. under nitrogen atmosphere, and conduct stirring operations for 10-12 hours. And detect the end of reactions with TLC. Reduce the pressure and recycle the solvent, and recrystallize the obtained yellow grease with ethyl acetate and n-hexane (2:1, V/V), and make vacuum drying to obtain faint yellow solid, 6-(3-N,N-dimethylammonium-2-fluoro-2-acrylketone-1-yl)-4-fluoro-1-isopropyl-2-methyl-1H-benzimidazole (II) 2.7 g, the yield rate is 87.9%; $^1$H NMR (CDCl$_3$) 1.55 (d, 6H), 1.63 (s, 1H), 2.68 (m, 1H), 2.96 (s, 6H), 6.78 (s, 1H), 7.45 (s, 2H); mass spectrum (EI): m/z 308 (M+H).

Embodiment IX [Guanidination Reaction]:

Add 5-(4-ethyl-piperazine-1-yl methyl)-2-aminopyridine (VIII) (2.2 g, 10 mmol) and anhydrous ethyl alcohol 25 mL into the reaction flask, low the temperature to 0° C., and add 65% nitric acid 0.45 mL and 50% cyanamide aqueous solution (1 mL, 12 mmol) in sequence, and then, raise the temperature slowly to 80° C., and conduct stirring reaction for 8-12 hours. Lower the temperature to 0° C., and again add 65% nitric acid 0.45 mL and 50% cyanamide aqueous solution (1 mL, 12 mmol), and then raise the temperature slowly to 80° C., and conduct stirring operations again for 6-8 hours, and detect completion of the reaction with TLC sampling. Lower the temperature to room temperature, and there will be precipitation. Make filtration, and recrystallize the filter cake with ethyl acetate and n-hexane (2:1, V/V) mixed solvent, and make vacuum drying to obtain luminous yellow solid N-[5-(4-ethyl-piperazine-1-yl methyl)pyridine-2-yl]guanidine nitrate (IX) 2.8 g, the yield rate is 86.2%; mass spectrum (EI): m/z 326 (M+H).

Embodiment X [Tertiary Cyclization Reaction]:

Add N-[5-(4-ethyl-piperazine-1-yl-methyl)pyridine-2-yl] guanidine nitrate (IX) (3.6 g, 11 mmol), 6-(3-N,N-dimethylammonium-2-fluoro-2-acrylketone-1-yl)-4-fluoro-1-isopropyl-2-methyl-1H-benzimidazole (II) (3.1 g, 10 mmol), sodium hydroxide (0.6 g, 15 mmol) and solvent n-butanol 25 mL into the reaction flask, and under nitrogen atmosphere, raise the temperature slowly to 90-100° C., and conduct stirring operations for 12-16 hours. And detect the end of reactions with TLC. Make natural cooling to room temperature, and there will be solid precipitation. Recrystallize with ethyl alcohol and water (1:2, V/V), and make vacuum drying to obtain off-white solid, Bemaciclib (I) 3.7 g, the yield rate is 73.1%; $^1$H NMR (DMSO-d$_6$) 1.16 (t, 3H), 1.62 (m, 6H), 2.51 (q, 2H), 2.64 (s, 3H), 2.68-2.73 (m, 4H), 2.83-3.04 (m, 4H), 3.52 (s, 2H), 4.65 (m, 1H), 7.12-7.21 (m, 2H), 7.45-7.64 (m, 2H), 8.21-8.27 (m, 2H), 9.07 (s, 1H); mass spectrum (EI): m/z 507 (M+H).

It needs to be noted that the above-mentioned embodiments are only used to describe the technical thought and characteristics of the invention and the purposes are to get the persons familiar with this technology understand the content of the invention and implement the invention accordingly. They shall not be used to restrict the protection scope of this invention. All equivalent changes and modifications made upon the spiritual essence of the invention shall be included in the protection scope of the invention.

What is claimed is:

1. A bemaciclib intermediate of Formula (II):

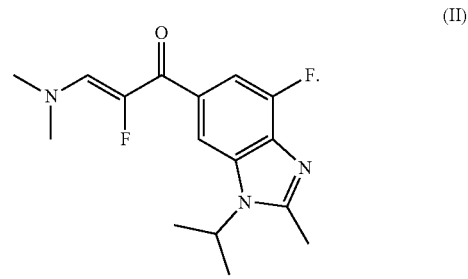 [SMILES: Cc1nc2c(F)cc(C(=O)/C(F)=C/N(C)C)cc2n1C(C)C]

* * * * *